(12) United States Patent
Bennett

(10) Patent No.: US 7,510,521 B2
(45) Date of Patent: Mar. 31, 2009

(54) SOUND AND HEARTBEAT PLAYBACK SYSTEM

(76) Inventor: James Bennett, 380 Myrtle, Laguna Beach, CA (US) 92651

( * ) Notice: Subject to any disclaimer, the term of this patent is extended or adjusted under 35 U.S.C. 154(b) by 442 days.

(21) Appl. No.: 10/679,094

(22) Filed: Oct. 3, 2003

(65) Prior Publication Data

US 2004/0068158 A1 Apr. 8, 2004

Related U.S. Application Data

(60) Provisional application No. 60/415,941, filed on Oct. 3, 2002.

(51) Int. Cl.
*A61M 21/00* (2006.01)
(52) U.S. Cl. ...................................................... 600/28
(58) Field of Classification Search ............ 600/26–28, 600/21, 559; 434/320
See application file for complete search history.

(56) References Cited

U.S. PATENT DOCUMENTS

| 4,969,867 | A | * | 11/1990 | Cohen | 600/28 |
| 5,183,457 | A | * | 2/1993 | Gatts et al. | 600/21 |
| 6,004,259 | A | * | 12/1999 | Sedaros | 600/28 |
| 6,256,965 | B1 | * | 7/2001 | Sheridan | 53/436 |
| 6,692,330 | B1 | * | 2/2004 | Kulick | 446/297 |
| 2002/0120176 | A1 | * | 8/2002 | Coviello | 600/28 |

* cited by examiner

*Primary Examiner*—Charles A Marmor, II
*Assistant Examiner*—Christine D Hopkins
(74) *Attorney, Agent, or Firm*—McAndrews, Held & Malloy, Ltd.

(57) ABSTRACT

Certain aspects of the invention may be found in a sound and heartbeat playback system that selectively generates and/or plays back sounds and/or heartbeats that mimic a natural mother's sounds and heartbeats. In this regard, the generation of heartbeat or other soothing and calming sounds may be incorporated into toys. The sound and heartbeat playback system may therefore be employed in a surrogate mother toy, for example, a cuddly bear with which infants may usually cuddle, play and/or sleep. Accordingly, the sound emitted by the sound and heartbeat playback system may aid in calming infants when they are agitated and/or tired.

18 Claims, 3 Drawing Sheets

SOUND AND HEARTBEAT PLAYBACK SYSTEM

CROSS-REFERENCE TO RELATED APPLICATIONS/INCORPORATION BY REFERENCE

This application makes reference to, claims priority to, and claims the benefit of: U.S. Provisional Application Ser. No. 60/415,941 filed on filed Oct. 3, 2002.

The above stated application is incorporated herein by reference in its entirety.

FIELD OF THE INVENTION

This invention generally relates to toys used by children and more specifically to toys that playback a mother's heartbeat or other familiar sounds of the mother, which is utilized to soothe or calm children.

BACKGROUND OF THE INVENTION

At least until the age of six to eight months, the sounds of a mother's voice and associated contact has a calming effect on most infants when they are agitated. In addition, infants like to be held close by their caregivers, typically the mother. The sound of the mother's heartbeat is expected to not only to calm infants when they are agitated but also to put them to sleep when they are tired.

When an infant is agitated and starts to cry, giving a toy to the infant may help in calming the infant. Similarly, when an infant is tired and needs to go to sleep, giving a toy to the infant sometimes helps the infant fall asleep. Part of the reason seems to be the role of a toy as a surrogate for the mother.

Experience and studies have also shown that having a calm baby, especially in times when mother and/or baby are tired can particularly result in a less stressful care giving experience for both mother and baby. Furthermore, first time mothers and postpartum mothers can sometimes get very frustrated and overwhelmed when a tired or achy baby does not readily fall asleep. Additionally, mothers with newborn babies and even some experienced mothers who get easily stressed due to an agitated baby are less likely to provide a nurturing and positive environment for the care of a baby.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

Certain embodiments of the invention provide a method and system for soothing or calming a child. Aspects of the method for soothing or calming a child may comprise receiving at least one triggering event by an audio enabled toy and selecting from within the audio enabled toy, at least one soothing sound that mimics a mother's sounds based on the triggering event. The sound may be, for example, a sound corresponding to a mother's heartbeat, or a tune, humming or lullaby in the mother's familiar voice. An audio signal representing the soothing sound may be generated and sound corresponding to the generated audio signal may be played from within the audio enabled toy.

The method may further comprise the step of determining whether the audio enabled toy should operate in a power down mode, a power saving mode and/or a normal operating mode subsequent to playing the sound corresponding to the generated audio signal. The triggering event may be a manual trigger and/or an automatic trigger wherein the manual trigger may be a signal corresponding to the push of a button and the automatic trigger may be a signal generated by a microphone. Notwithstanding, an operational mode may be determined from within the audio enabled toy based on the received triggering event. The operational mode may be, for example, a decreasing heart beat mode, an increasing heart mode, a constant heartbeat mode and a miscellaneous sounds mode consisting of different sounds. A duration, volume and/or pitch, for example, of the audio representation of the soothing sound may be varied from within the audio enabled toy. In another embodiment of the invention, soothing sounds generated by a microphone coupled to the audio enabled toy may be recorded and stored within the audio enabled toy in a memory unit. At least some of the soothing sounds may also be in a mother's familiar voice.

Another embodiment of the invention may provide a machine-readable storage, having stored thereon, a computer program having at least one code section for soothing or calming a child. The at least one code section may be executable by a machine, thereby causing the machine to perform the steps as described above for soothing and calming a child.

Another aspect of the invention may provide a system embodied in a toy that may be utilized for soothing or calming a child. The system may comprise a processing circuit that receives at least one triggering event by an audio enabled toy and selects from within the audio enabled toy, at least one soothing sound that mimics a mother's sound based on the triggering event. The processing circuit and/or an audio output unit may be adapted to generate an audio representation of the soothing sound. The audio output unit may play from within the audio enabled toy via a speaker coupled to the audio output unit, sounds corresponding to the generated audio signal. The processing circuit and/or a mode control unit may be configured to determine whether the audio enabled toy should operate in a power down mode, a power saving mode and/or a normal operating mode subsequent to playing sounds corresponding to the generated audio signal.

In accordance with an embodiment of the invention, the triggering event may be a manual trigger and/or an automatic trigger, wherein the manual trigger may be a signal corresponding to the push of a button and the automatic trigger may be a signal generated by a microphone. Notwithstanding, the processing circuit may determine from within the audio enabled toy, an operating mode based on the received triggering event. In this regard, the operating mode may be, for example, a decreasing heart beat mode, an increasing heart mode, a constant heartbeat mode, a constant heartbeat mode and a miscellaneous sounds mode. A timer may be utilized to vary from within the audio enabled toy, a duration of the soothing sound. A volume control unit may also be utilized to vary a volume and/or a pitch of the audio representation of the soothing sound. The system may further comprise a memory coupled to the processing circuit and/or the audio output unit, which may be utilized to store at least one soothing sound generated by the microphone coupled to the audio enabled toy and/or by the sound generator. At least some of the sounds generated by the microphone may be in a mother's familiar voice.

In a further embodiment of the invention, a system embodied in a toy for soothing and calming a child may comprise a switch coupled to a processing circuit and a timer, and a mode control unit and/or a volume control unit coupled to the processing circuit. An audio output unit may be coupled to the processing circuit and the audio output unit may comprise at least one sound generator. The sound generator may include a heartbeat sound generator and/or another sound generator that may be utilized to generate other soothing and calming sounds. The audio enabled toy may include an integrated speaker which may be coupled to the audio output unit. A microphone and memory may also be coupled to the processing circuitry and/or the audio output unit.

These and other advantages, aspects and novel features of the present invention, as well as details of an illustrated embodiment thereof, will be more fully understood from the following description and drawings.

DETAILED DESCRIPTION OF THE INVENTION

Certain aspects of the invention may be found in a sound and heartbeat playback system that may be adapted to selectively generate and/or play back sounds and/or heartbeats that mimics a natural mother's sounds and heartbeats. The generation of heartbeat and other soothing or calming sounds may be incorporated into a toy such as a surrogate mother toy embodied, for example, in a cuddly bear. Accordingly, sounds emitted by the sound and heartbeat playback system may aid in calming infants when they are agitated and/or tired.

Certain embodiments of the invention may also be found in a method and system for soothing or calming a child. Certain aspects of the method for soothing or calming a child may comprise receiving at least one triggering event by an audio enabled toy and selecting from within the audio enabled toy, at least one soothing sound that mimics a mother's sounds based on the triggering event. The sound may be a heartbeat, for example. An audio signal representing the soothing sound may be generated and sound corresponding to the generated audio signal played from within the audio enabled toy.

Figure 1:
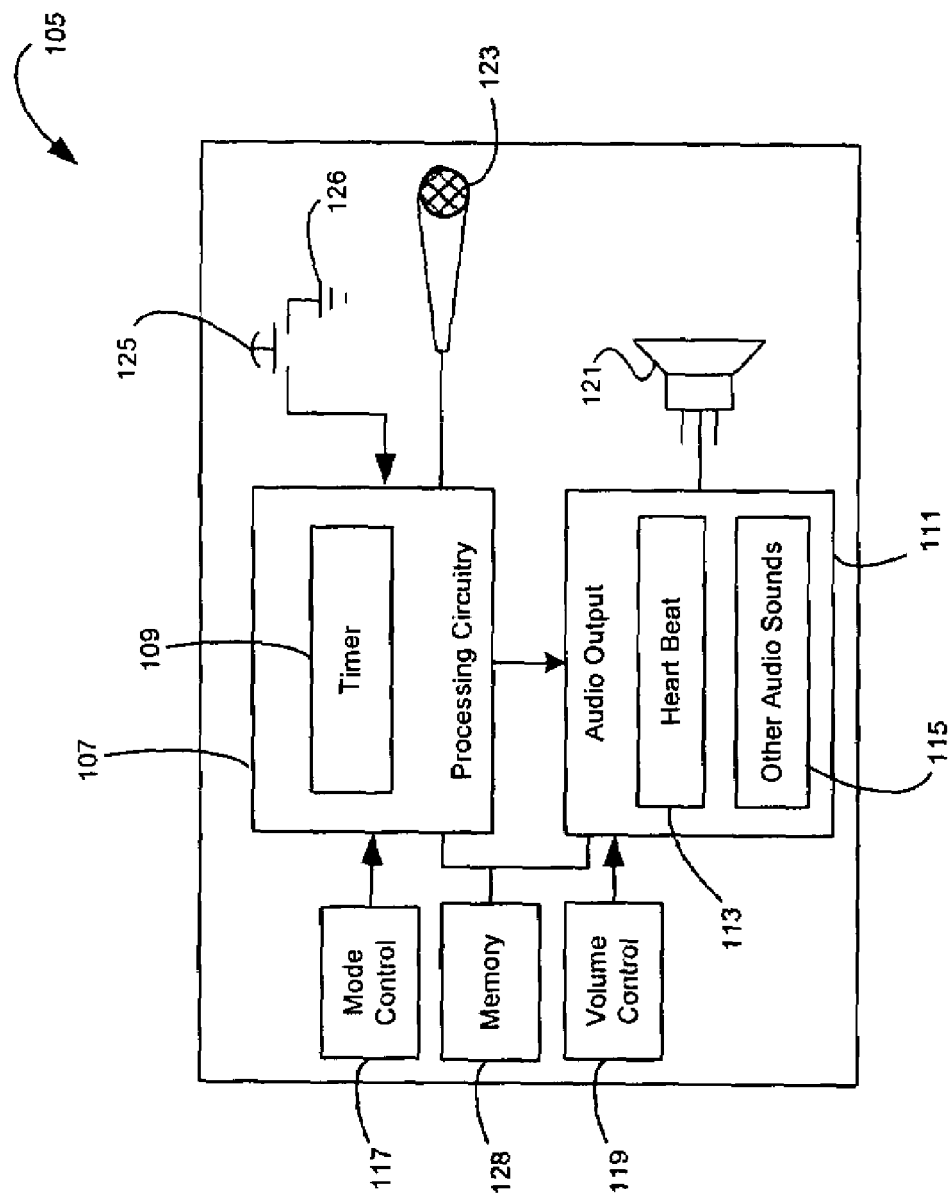
FIG. 1 is perspective block diagram of a sound and heartbeat playback system 105 that selectively plays back sounds and heartbeats that mimics a natural mother's sounds and heartbeats, the sound and heartbeat playback system capable of being employed in a surrogate mother toy, in accordance with an embodiment of the invention.

FIG. 1 is perspective block diagram of a sound and heartbeat playback system 105 that selectively plays back sounds and heartbeats that mimics a natural mother's sounds and heartbeats, the sound and heartbeat playback system capable of being employed in a surrogate mother toy, in accordance with an embodiment of the invention. Referring to FIG. 1, the sound and heartbeat playback system 105 may comprise a processing circuit or circuitry 107, an audio output unit 111, a memory 128, a voltage source 125, a switch 126, a speaker 121, a mode control unit 117 and a volume control unit 119. Except for the voltage source 125, the speaker 121 and the switch 126, at least some of the other components of the playback system 105 may be embodied in a single chip. In this regard, processing circuitry 107, audio output unit 111, the mode control unit 117 and/or the volume control unit 119 of the playback system 105 may be integrated into at least a single chip or ASIC.

The processing circuitry may comprise a timer circuitry 109. The processing circuitry 107 may include suitable circuitry and/or logic that may be adapted to control the audio output unit 111 based on settings established by the mode control unit 117. The timer 109 may be adapted to provide heartbeat rate information to the audio output unit 111 and to control the rate at which heart beats are provided by the audio output unit 111 based on various modes. In general the timer 109 may include suitable circuitry and/or logic that may be adapted to control, for example, a pulse voltage and/or pulse current supplied to the audio output unit 111. The timer 109 may also be adapted to control a duration for playing heartbeats and/or other sounds generated by the sound and heartbeat playback system 105.

The memory 128 may comprise a ROM portion and a RAM portion. The ROM portion of the memory 128 may be, for example a PROM or an EEPROM and the RAM portion may be, for example, a DRAM. The memory 128 may also comprise a FLASH memory. Notwithstanding, the ROM portion of the memory 128 may be adapted to store permanent operational data and/or operational code. The RAM portion of the memory 128 may also be adapted to store temporary operational data. Sounds such as heartbeats may also be stored in the ROM portion of the memory 128. The memory 128 may be coupled to the processing circuitry 107 and the audio output unit 111

The audio output unit 111 may comprise a heartbeat generator 113 and/or another audio sounds generator 115. The audio output unit 111 may be a microprocessor, a specialized processor or it may be implemented as an ASIC. Notwithstanding, the audio output unit 111 may be capable of selectively generating and/or playing back recorded and/or stored audio signals. The audio sounds generator 115 may be, for example, a sound generator that may be embodied in a single chip. The output of the sounds generator 111 may be controlled by the timer 109. In this regard, a pulse voltage and/or pulse current supplied by the timer 109 may control a duration, pitch and/or type of sound that may be generated by the other sounds generator 111.

The heartbeat generator 113 may be a sound generator circuit, which may be embodied in a chip, and may be adapted to selectively generate and/or play back heartbeat signals. The rate, pitch and/or duration at which the heart beat signals generated by the heart beat generator 113 may be varied by the timer 109.

The voltage source 125 may comprise, for example, a battery or a voltage adapter that may be adapted to receive an alternating current (AC) and convert the alternating current to direct current (DC). In the case of a battery, the voltage source may be a standardized source such as 1.5V, 3V, 6V and 9V. In this regard, the heartbeat playback system 105 may be adapted to utilize a standard battery or battery pack.

The switch 126 may comprise a toggle switch or a push button switch, for example. The switch 126 may be adapted to cause a voltage difference to be setup when depressed, thereby causing a current to flow to the processing circuitry.

The speaker 121 may comprise a speaker unit that may be configured in a monaural or stereo mode or other enhanced audio processing mode. The speaker 121 may be coupled to the audio output unit 111. Accordingly, digital and/or analog signals processed by the processing circuitry 107 and/or the audio output unit 113 may be played back and heard via the speaker unit 107. The speaker unit 121 may be integrated within the heartbeat playback system 105 and may also be optionally coupled to the audio output unit 111 via a connector that may be integrated on the surface of the heartbeat playback system 105. The speaker unit 121 may also include suitable audio conditioning and/or amplification circuitry that may be adapted to condition and/or amplify audio signals that may be received from the audio output unit 111 to provide an enhanced sound quality and listening experience.

The mode control unit 117 may comprise a multimodal switch that may be adapted to control or set one of several possible modes of operation. In one aspect of the invention, the possible modes of operation for the mode control unit 117 may include, but are not limited to, a decreasing heartbeat mode, an increasing heartbeat mode, a steady heartbeat mode and an other or miscellaneous sounds mode.

The volume control unit 119 may comprise a resistor or variable resistor that may be adapted to control an audio level of output audio signals generated by the audio output unit 111. The volume control 119 may be adapted to control the volume of a heartbeat sound and/or other audio sounds that may be generated and/or played back by the audio output unit 111.

The microphone 123 may be utilized to receive an analog voice input and convert the input into in a digital or analog audio signal that may be received and processed by the processing circuitry 107. In an aspect of the invention, the microphone 123 may be configured to selectively trigger the playback of heartbeats and/or other sounds by the audio output unit 111. Also, audio inputs received via the microphone 123 may be converted to digital format and saved for subsequent playback. For example, the microphone 111 may be utilized to record a mother's heartbeats for subsequent playback at times when a child may be tired and/or agitated. The microphone 123 may also be utilized to save voice inputs from a user to be stored and subsequently played back.

In operation, in one embodiment of the invention, the sound and heartbeat playback system 105 may be adapted to record audio signals representing heartbeats of a person such as a mother, and store data representative of the recorded heartbeat in the memory 128 for subsequent playback. The sound and heartbeat playback system 105 may also receive audio trigger signals from an external environment and, in response, may play back sounds and/or heartbeats, such heartbeats either previously recorded for playback or selectively generated by the audio output unit 111. The previously recorded sounds and/or heartbeats may be retrieved from the memory 128 for playback. Sounds generated from the microphone 123 and/or via a push of the button 125 may cause the sound and heartbeat playback system 105 to start playing, for example, heartbeat sounds at a decreasing heartbeat rate. In this regard, the timer 109 may generate a signal to control the audio output unit 111, there causing the audio output unit 111 to generate a decreasing heartbeat rate signal that is sent to the speaker 121. In another aspect of the invention, the sound and heartbeat playback system 105 may receive a signal to start playing back the heartbeat at a decreasing rate. In response to receiving this signal, the sound and heartbeat playback system 105 may play back the heartbeat at a decreasing rate utilizing the audio output unit 111 and the speaker 121. The microphone and/or the button 125 may be utilized to initiate playback of the heartbeat at the decreasing rate. The sound and heartbeat playback system 105 may also be adapted to playback a heartbeat at a constant rate.

The sound and heartbeat playback system 105 may also utilize the other audio sounds generator 111 to playback plays other audio sounds, such sounds that may have been previously recorded utilizing the microphone 123. These other sound may also be generated by the other audio sounds generator 115 or may have been previously digitized and stored in the memory 128.

In one embodiment of the invention, the sound and heartbeat playback system 105 may be embodied in a toy to provide soothing or calming sounds and/or heartbeats to, for example, infants, children, and mothers who use the toy. Soothing or calming sounds such as waterfalls and birds chirping may also be utilized to provide a relaxing atmosphere or mood. The toy may be, for example, a fluffy bear which may comprise a microphone, a power source such as a battery, and at least one button to start/stop or change and/or set an operating mode for the sound and heartbeat playback system 105. A mode button, which controls the mode control unit 117, may also be provided to select between various preset or user defined modes of operation. Accordingly, the toy bear may selectively play heartbeats in increasing, decreasing or at a constant rate. The playback and/or generation of the heartbeats and/or other sounds may be selectively triggered by external sounds and/or signals that may be received by, for example, the microphone based on the modes established by the mode control unit 117. In an embodiment of the invention, the sound and heartbeat system 105 may include a motion sensor that is adapted to trigger playback whenever the toy may be moved. In another embodiment of the invention, the sound and heartbeat system 105 may include a noise sensor that may be configured to detect when a baby is crying and may start playback whenever a baby cries.

The sound and heartbeat playback system 105 that selectively plays back sounds and/or heartbeats that mimics a natural mother's sounds and heartbeats makes it possible to incorporate heartbeat generation, or the generation of other soothing or calming sounds into toys. The sound and heartbeat playback system is capable of being employed in a surrogate mother toy, such as a cuddly bear, which infants usually play with or sleep with. Sounds generated and emitted by the heartbeat playback system 105 may calm infants when they are agitated and/or tired and will assist in putting them to sleep.

Figure 2:
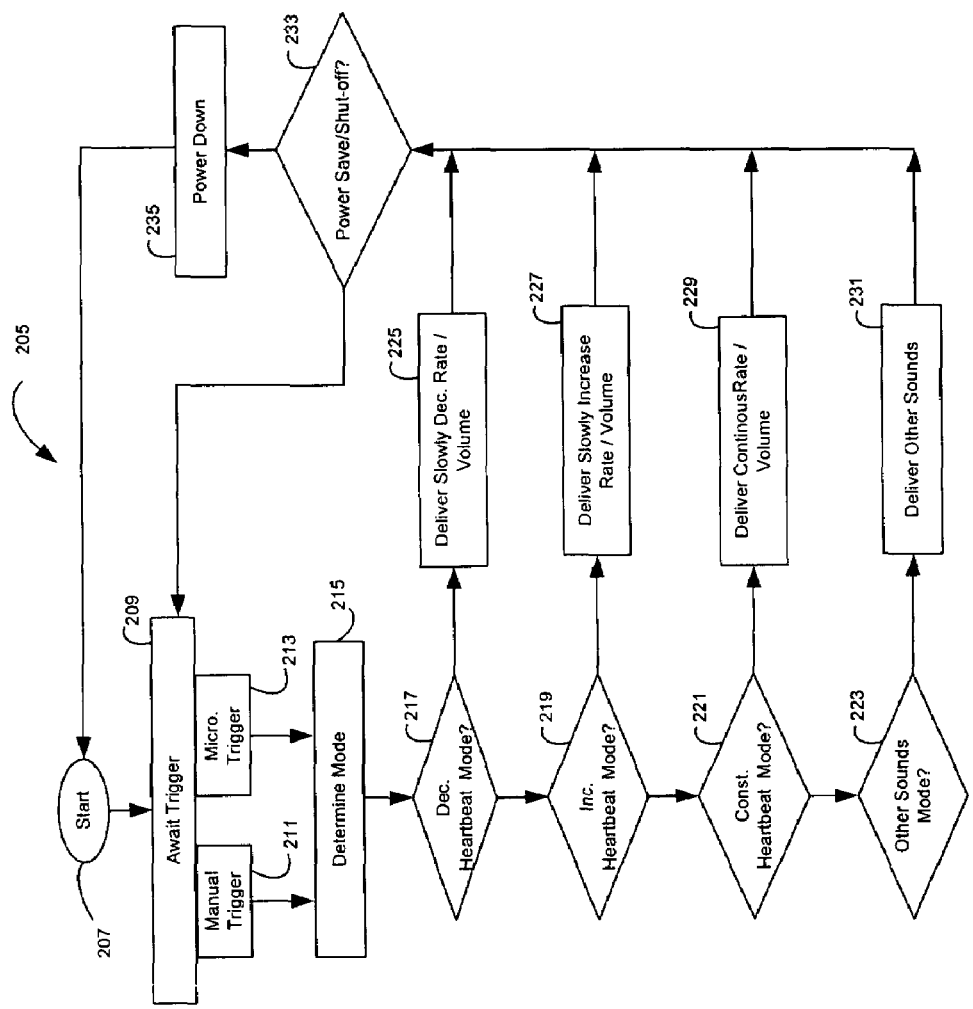
FIG. 2 is a flow chart 205 of exemplary processing steps that may be utilized by the heartbeat playback system 105 in accordance with and embodiment of the invention.

FIG. 2 is a flow chart 205 of exemplary processing steps that may be utilized by the heartbeat playback system 105 in accordance with and embodiment of the invention. Referring to FIG. 2, the exemplary steps begin with step 207, typically when the heartbeat playback system is powered on. In step 209, the sound and heartbeat playback system waits for a trigger and is in a trigger mode. The trigger may be generated manually by user activation of a button or contact, or automatically when the microphone senses input signals indicating a user input or user activation. The trigger mode may typically be configured by the user employing appropriate switches and/or settings.

In step 209, if a manual trigger is sensed or detected by the manual trigger 211, or the automatic trigger 213 detects a trigger from the microphone, processing proceeds to the step 215. In step 215, the mode settings that control the output of heartbeats and/or sounds may be determined. In one embodiment of the invention, the mode settings may be an increasing heartbeat, a decreasing heartbeat, a constant heartbeat or some other sound. In step 217, if it is determined that the current mode is a decreasing heartbeat, a transition is made to the step 225. Accordingly, in step 225, an audio signal is generated representing a slowly decreasing rate of heartbeat and is delivered to the speaker(s) for output. Otherwise, control passes to step 219.

In step 219, if it is determined that the current mode is an increasing heartbeat, a transition is made to the step 227 where an audio signal is generated representing a slowly increasing rate of heartbeats, which is delivered to the speaker(s) for output. The rate of the heartbeats may be increased up to a preset maximum rate or a default rate value, for example. Otherwise, control passes to the step 221.

In step 221, if it is determined that the current mode is a continuous heartbeat, a transition is made to step 229 where an audio signal is generated representing a continuous or steady rate of heartbeats, which is delivered to the speaker(s) for output. Otherwise, control passes to the step 223.

In step 223, if it is determined that the current mode is to deliver other sounds, a transition is made to step 231 where some other sound which was previously recorded is delivered to the speaker(s) for output. Generation and delivery of the other sounds mode may be referred to as a miscellaneous mode. In another aspect of the invention, the other sound may be automatically generated based on settings, for example, and the generated sound may be delivered to the speaker(s) for output.

For at least some of the modes, after commencement of the delivery of heartbeats or sounds, a duration of the delivered heartbeats or sounds may be determined by a user setting or a default setting. In accordance with an embodiment of the invention, a power save mode may be entered once the user specified duration or the default duration has expired. In this regard, power to the heartbeat playback system may be shut-off or the heartbeat playback system may return to a state where it awaits a new trigger. Accordingly, subsequent to steps 225, 227, 229, and 231, in step 233, if it is determined that the heartbeat playback system needs to be powered off due to user intervention, for example, then, the heartbeat playback system may be powered down in step 235. In this regard, the heartbeat playback system may have to be restarted in step 207. However, in power save mode or normal operation mode, operation of the heartbeat playback system may return to step 215, where the heartbeat playback system waits for another trigger to occur.

Figure 3:
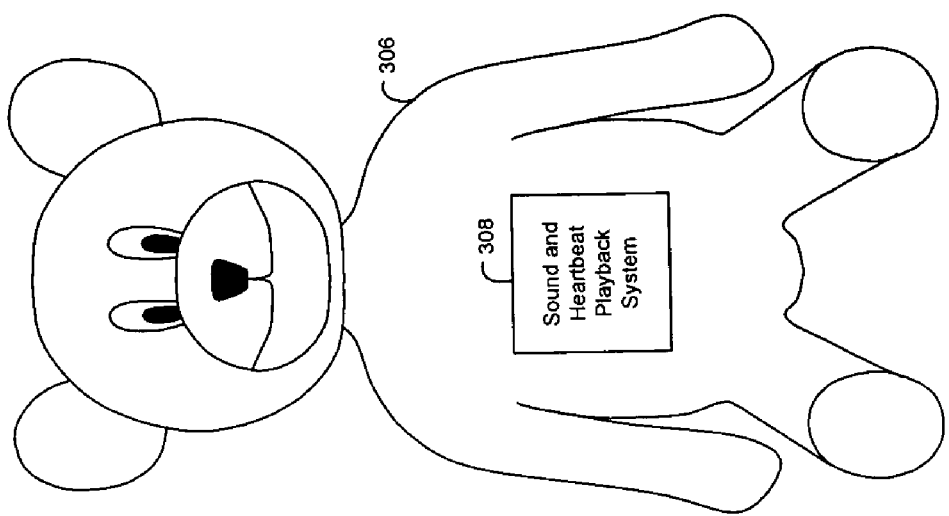
FIG. 3 is diagram of an exemplary system for a surrogate mother toy in accordance with an embodiment of the present invention.

FIG. 3 is diagram of an exemplary system for a surrogate mother toy in accordance with an embodiment of the present invention. Referring to FIG. 3, there is shown toy in the form of a bear 306 having integrated therein, a sound and heartbeat playback system 308. The sound and heartbeat playback system 308 may be similar to the exemplary sound and heartbeat playback system 105 of FIG. 1. Although the surrogate mother toy of FIG. 3 is illustrated as a teddy bear, the invention is not so limited and other types of toys such as those that are loved by children may be utilized. For example, the sound and heartbeat playback system 105 may be embodied in a mouse, a rabbit, a pig or other character or animal.

Accordingly, the present invention may be realized in hardware, software, or a combination of hardware and software. The present invention may be realized in a centralized fashion in one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for soothing or calming a child, the method comprising:
   receiving in an audio enabled toy comprising a handheld stuffed animal, a first signal caused by a first at least one external triggering event;
   determining from within said audio enabled toy, a first playback operating mode from a plurality of playback operating modes based on said received first signal caused by said first at least one external triggering event, wherein said plurality of playback operating modes comprises a constant heartbeat mode, an increasing heartbeat mode and a decreasing heartbeat mode;
   selecting by said audio enabled toy, at least one sound that mimics a mother's sound from a plurality of mother's sounds based on said determined playback operating mode;
   generating an audio signal representing said at least one sound;
   receiving in said audio enabled toy, a second signal caused by a second at least one external triggering event;
   determining from within said audio enabled toy, a second playback operating mode from said plurality of playback operating modes based on said received second signal caused by said second at least one external triggering event; and
   changing said first playback operating mode to said second playback operating mode.

2. The method according to claim 1, further comprising playing by said audio enabled toy, sound corresponding to said generated audio signal.

3. The method according to claim 2, further comprising determining whether said audio enabled toy should operate in at least one of a power down mode, a power saving mode and a normal operation mode subsequent to said playing of said sound corresponding to said generated audio signal.

4. The method according to claim 1, wherein at least one of said first at least one external triggering event and said second at least one external triggering event is at least one of a manual trigger and an automatic trigger.

5. The method according to claim 4, wherein manual trigger is a signal corresponding to the push of a button and said automatic trigger is a signal generated by a microphone.

6. The method according to claim 1, wherein said plurality of playback operating modes further comprises a miscellaneous sounds mode.

7. The method according to claim 1, further comprising varying from within said audio enabled toy, at least one of a duration, a volume and a pitch of said audio representation of said sound.

8. The method according to claim 1, further comprising recording at least one sound generated by a microphone coupled to said audio enabled toy.

9. The method according to claim 8, further comprising storing said recorded at least one sound within said audio enabled toy.

10. A system embodied in a toy for soothing or calming a child, the system comprising:
   a processing circuit of an audio enabled toy comprising a handheld stuffed animal, that receives a first signal caused by a first at least one external triggering event;
   said processing circuit determines a first playback operating mode from a plurality of playback operating modes based on said received first signal caused by said first at least one external triggering event and selects from within said audio enabled toy, at least one sound that mimics a mother's sound from a plurality of mother's sounds based on said determined playback operating mode, wherein said plurality of playback operating modes comprises a constant heartbeat mode, an increasing heartbeat mode and a decreasing heartbeat mode; and
   at least one of said processing circuit and an audio output unit generates an audio signal representing the at least one sound,
   wherein said first playback operating mode is changed to a second playback operating mode determined by said processing circuit from said plurality of operating modes based on a received second signal caused by a second at least one external triggering event.

11. The system according to claim 10, wherein said audio output unit plays from within said audio enabled toy and via a speaker coupled to said audio output unit, sounds corresponding to said generated audio signal.

12. The system according to claim 11, wherein at least one of said processing circuit and a mode control unit determines whether said audio enabled toy should operate in at least one of a power down mode, a power saving mode and a normal operating mode subsequent to said playing of said sounds corresponding to said generated audio signal.

13. The system according to claim 10, wherein at least one of said first at least one external triggering event and said second at least one external triggering event is at least one of a manual trigger and an automatic trigger.

14. The system according to claim 13, wherein manual trigger is a signal corresponding to the push of a button and said automatic trigger is a signal generated by a microphone.

15. The system according to claim 10, wherein said plurality of playback operating modes further comprises a miscellaneous sounds mode.

16. The system according to claim 10, further comprising:
   a timer that varies from within said audio enabled toy, a duration of said soothing sound; and
   a volume control unit varies at least one of a volume and a pitch of said audio representation of said at least one sound.

17. The system according to claim 10, further comprising a memory coupled to at least one of said processing circuit and said audio output unit for storing at least one sound generated by at least one of a microphone coupled to said audio enabled toy and sound generator.

18. A system embodied in a toy for soothing and calming a child, the system comprising:
   a switch having a plurality of switch settings and coupled to a processing circuit, wherein each of a plurality of playback operating modes is associated with a different one of said plurality of switch settings;
   at least one of a timer and a volume control unit coupled to said processing circuit;
   a mode control unit coupled to said processing circuit for determining a playback operating mode from said plurality of playback operating modes based on a selected switch setting of said plurality of switch settings, wherein said plurality of playback operating modes comprises a constant heartbeat mode, an increasing heartbeat mode and a decreasing heartbeat mode; and
   an audio output unit coupled to said processing circuit, said audio output unit comprising at least one sound generator capable of generating at least one of heartbeats and voice sounds of a mother;
   a speaker integrated within the handheld toy and coupled to said audio output unit; and
   a microphone and memory coupled to at least one of said processing circuitry and said audio output unit.

* * * * *